United States Patent
Lee et al.

(10) Patent No.: US 6,893,860 B1
(45) Date of Patent: May 17, 2005

(54) MICROORGANISMS AND METHODS FOR PRODUCING THREONINE

(75) Inventors: Hyo Hoon Lee, Kyongki-do (KR); Jae Chun Han, Seoul (KR); Tae Man Jung, Seoul (KR)

(73) Assignee: Daesang Corporation, Seoul (KR)

( * ) Notice: Subject to any disclaimer, the term of this patent is extended or adjusted under 35 U.S.C. 154(b) by 0 days.

(21) Appl. No.: 10/069,825

(22) PCT Filed: Aug. 26, 1999

(86) PCT No.: PCT/KR99/00488

§ 371 (c)(1),
(2), (4) Date: Jun. 28, 2002

(87) PCT Pub. No.: WO01/14525

PCT Pub. Date: Mar. 1, 2001

(51) Int. Cl.[7] .................................................. C12N 1/20
(52) U.S. Cl. ................ 435/252.8; 435/115; 435/252.33
(58) Field of Search ......................... 435/252.8, 252.33, 435/115

(56) References Cited

FOREIGN PATENT DOCUMENTS

ZA             9810327        *    7/1998

* cited by examiner

Primary Examiner—Herbert J. Lilling
(74) Attorney, Agent, or Firm—Martine & Penilla, LLP

(57) ABSTRACT

The present invention relates to methods and microorganisms for producing L-threonine. In particular, the present invention relates to the production of L-threonine using microorganisms, and *Escherichia coli* strains in particular, which require L-methionine for growth and are L-isoleucine-leaky, are resistant to α-methylserine, diaminosuccinic acid, L-glutamic acid, L-threonine, medium containing 60% of L-threonine fermentation mother liquid, azetidine and dehydroproline, and which are susceptible to fluoropyruvate.

2 Claims, No Drawings

MICROORGANISMS AND METHODS FOR PRODUCING THREONINE

BACKGROUND OF THE INVENTION

1. Field of the Invention

The present invention relates to microorganisms and methods for producing L-threonine. In particular, the present invention relates to the production of L-threonine using microorganisms, and *Escherichia coli* strains in particular, which require L-methionine, are L-isoleucine-leaky for growth, are resistant to α-methylserine, diaminosuccinic acid, L-glutamic acid, L-threonine, medium containing 60% of L-threonine fermentation mother liquid (which contains more than 9.0% threonine), azetidine and dehydroproline, and which are susceptible to fluoropyruvate.

2. Description of the Related Art

L-threonine, an essential amino acid, is a second limited amino acid of rice. As is well known, 1-threonine is used as a component for, e.g., amino acid transfusion liquid or general amino acid tablets, and as a nutrient. Recently, there has been a great increase in the demand for L-threonine because it, together with L-lysine, is used as an additive in feedstuff.

Japanese Pat. Publication No. Heisei 5-10076 teaches use of recombinant DNA which contains the genetic information for asparto kinase, homoserine kinase, homoserine dehydrogenase, and threonine synthase in production of threonine from a L-threonine-producing *Serratia* sp. Japanese Pat. Publication No. Heisei 1-289493 discloses that a DNA taken from a *Providencia* sp. resistant to methionine metabolic antagonist is genetically engineered and used to increase the productivity of L-threonine. In order to produce L-threonine, a threonine metabolic antagonist-resistant *Escherichia* sp. which requires methionine or diaminopimelic acid for growth has been used (Japanese Pat. Publication No. Sho. 56-10037). A strain which can grow in medium containing L-serine and ethionine has also been used (EP 91103569.9).

SUMMARY OF THE INVENTION

The present invention relates to novel microorganisms and methods of producing large quantities of L-threonine using the microorganisms. The present microorganisms are derived from the microorganism deposited in the Korean Culture Center of Microorganisms, College of Engineering, Yonsei University, Sodaemun gu, Seoul 120-749, Republic of Korea, on Jul. 16, 1998, having the deposition number KCCM-10132. KCCM-10132 has also been described in PCT Application Number PCT/KR 98100340.

KCCM-10132, the parent strain of the present microorganisms, requires both L-methionine and L-isoleucine, is resistant to α-methylserine, diaminosuccinic acid, L-glutamic acid and L-threonine, and is susceptible to fluoropyruvate. KCCM 10132 also requires diaminopimelic acid.

To obtain the present microorganisms, KCCM-10132 was mutated and cells which were resistant to L-threonine, able to grow on medium containing 60% of L-threonine fermentation mother liquid (which contains more than 9.0% threonine), azetidine and dehydroproline were selected. As used herein, the terminology "able to grow on medium containing L-threonine fermentation mother liquid" means that the microorganism is able to grow on minimal agar plates which contain the production medium for the parent strain KCCM10132, the ingredients of which are listed in Example 2. The production medium for the parent strain KCCM 10132 contains glucose at a concentration of 10%, corn steep liquor at a concentration of 3%, potassium dihydrogen phosphate at a concentration of 0.1%, ferrous sulfate at a concentration of 2 mg/ℓ, manganese sulfate at a concentration of 2 mg/ℓ, ammonium sulfate at a concentration of 0.05%, urea at a concentration of 0.6%, L-methionine at a concentration of 200 mg/ℓ and pH 7.0 and L-isoleucine at a concentration of 200 mg/ℓ. To prepare the "L-threonine fermenation mother liquid" the parent strain KCCM10132 is grown in the preceding medium for 100 hours at 30 degrees Celsius. When cultured in media containing a high concentration of glucose, the present microorganisms accumulate large quantities of L-threonine in the culture.

DETAILED DESCRIPTION OF THE PREFERRED EMBODIMENTS

The novel strain of the present invention, which has been deposited in the Korean Culture Center of Microorganisms and has been assigned deposit number KCCM-10168, can grow well in the presence of fermentation mother liquid in which the strain was grown, L-azetidine-2-carboxylic acid and 3,4-dehydro-DL-proline. In other words, KCCM-10168 is resistant to fermentation mother liquid in which the strain was grown, L-azetidine-2-carboxylic acid (hereinafter "azetidine") and 3.4-dehydro-DL-proline (hereinafter "dehydroproline").

As discussed above, KCCM-10168 was derived from a strain deposited at the Korean Culture Center of Microorganisms under deposit number KCCM-10132. The strains of the present invention may be obtained by treating KCCM-10132 with UV or with chemical mutagens, such as NTG (N'-methyl-N'-nitro-N-nitroso guanidine) and DES (diethylsulfate). Following mutagenesis, the cells were streaked on minimal agar plates containing 60% of L-threonine fermentation mother liquid (more than 9.0% of threonine) to select L-threonine fermentation mother liquid-resistant colonies.

The selected colonies were streaked on complete agar plates containing 60% of L-threonine fermentation mother liquid, 2 g/ℓ azetidine and 2 g/ℓ dehydroproline and cultured at 37° C. for 2–3 days. The complete agar plates included yeast extract. 1.0%, peptone 1.0%, beef broth 0.3%, NaCl 0.5% and glucose 0.5% at pH 7.0.

Thereafter, replicas of the colonies grown were made on a minimal agar plate containing 60% of L-threonine fermentation mother liquid, 2 g/ℓ azetidine and 2 g/ℓ dehydroproline and a minimal agar plate devoid of these components. Of the colonies which survived on the agar plate containing 60% of L-threonine fermentation mother liquid, 2 g/ℓ azetidine and 2 g/ℓ dehydroproline, those which were clearly grown were separated, and their characteristics were compared with those of the parent strain KCCM-10132. The minimal plates on which the microbiological properties of the mutant and parent strains were compared included 1.0% glucose, 0.2% ammonium sulfate, 0.1% potassium dihydrogen phosphate, 0.02% magnesium sulfate at pH 7.3, and 2% agar. Diaminopimelic acid at 100 mg/ℓ, L-methionine at 200 mg/ℓ and L-isoleucine at 200 mg/ℓ were respectively used in order to determine whether they were needed for the growth of the novel strain.

DSM9906 is a strain obtained using the above procedure. DSM9906 was deposited in the Korea Culture Center of Microorganisms, College of Engineering, Yonsei university, Sodaemun gu, Seoul 120-749, Republic of Korea, on Jul. 29, 1999 and was assigned Deposition No. KCCM-10168. While the Following discussion utilizes KCCM-10168 as an example of the microorganisms of the present invention, it will be appreciated that other strains, and in particular other *E. coli* strains, which have the properties of KCCM-10168 may be used to produce L-threonine. In particular, the *E. coli* strains may be derived from KCCM-10132. Alternatively, the microorganisms may be from species other than *E. coli*, including strains of *Brevibacteria* or *Corynebacteria*.

For example, to select a microorganism which requires L-methionine for growth, the microorganism is mutagenize as described above. After mutagenesis, the cells are streaked on complete agar plates comprising 1% yeast extract, 1% peptone, 0.3% beef broth, 0.5% NaCl, 0.5% glucose, and 2% agar at pH7.0. The colonies are replica plated on minimal plates containing 5.0% fructose, 1.4% ammonium sulfate, 0.2% potassium dihydrogen phosphate, 0.1% magnesium sulfate, a sufficient amount of any additional compounds required by the microorganism to permit growth, and 2% agar at pH 7.3 with or without L-methionine in order to identify colonies which grow in the presence of L-methionine but not in the absence of L-methionine. The L-methionine may be present at any concentration which is sufficient to differentiate strains which require L-methionine from strains which do not require L-methionine. For example, the L-methionine may be present at from about 50 mg/ℓ to about 400 mg/ℓ, preferably from about 100 mg/ℓ to about 300 mg/ℓ, and more preferably at about 200 mg/ℓ. Strains which grow in the presence of L-methionine but not in its absence may be used in conjunction with the present invention.

For example, to select a microorganism which is leaky for L-isoleucine, the microorganism is mutagenized as described above. After mutagenesis the cells are streaked on complete agar plates comprising 1% yeast extract, 1% peptone, 0.3% beef broth, 0.5 NaCl, 0.5% glucose, and 2% agar at pH7.0. The colonies are replica plated on minimal plates containing 5.0% fructose, 1.4% ammonium sulfate, 0.2% potassium dihydrogen phosphate, 0.1% magnesium sulfate, a sufficient amount of any additional compounds required by the microorganism to permit growth and 2% agar at pH 7.0 with or without L-isoleucine in order to identify colonies which grow slowly in the absence of L-isoleucine but which exhibit more robust growth in the presence of L-isoleucine. The L-isoleucine may be present at any concentration which is sufficient to identify strains which grow slowly in the absence of L-isoleucine from strains but which exhibit more robust growth in its presence. For example, growth on plates containing L-isoleucine at from about 50 mg/ℓ to about 400 mg/ℓ, preferably from about 100 mg/ℓ to about 300 mg/ℓ, and more preferably at about 200 mg/ℓ can be compared to growth on plates lacking L-isoleucine. Strains which grow slowly in the absence of L-isoleucine but more robustly in its presence may be used in conjunction with the present invention.

To select a microorganism which is resistant to α-methylserine, the microorganism is mutagenized as described above. After mutagenesis, the cells are streaked on complete agar plates comprising 1% yeast extract, 1% peptone, 0.3% beef broth, 0.5% NaCl, 0.5% glucose, α-methylserine and 2% agar at pH 7.0. The α-methylserine may be present at any concentration which is sufficient to differentiate strains which are resistant to α-methylserine from strains which are sensitive to α-methylserine. For example, growth on plates containing α-methylserine at from about 10 mM to about 200 mM, preferably from about 20 mM to about 100 mM, and more preferably at about 40 mM indicates that the strain is resistant to α-methylserine. The resulting colonies are then replica plated on minimal plates containing 5.0% fructose, 1.4% ammonium sulfate, 0.2% potassium dihydrogen phosphate, 0.1% magnesium sulfate, a sufficient amount of any additional compounds required by the microorganism to permit growth, and 2% agar at pH 7.3 with or without α-methylserine at the concentration used in the complete agar plates in order to identify colonies which are resistant to α-methylserine. Strains which grow in the presence of α-methylserine may be used in conjunction with the present invention.

To select a microorganism which is resistant to diaminosuccinic acid, the microorganism is mutagenized as described above. After mutagenesis, the cells are streaked on complete agar plates comprising 1% yeast extract, 1% peptone, 0.3% beef broth, 0.5% NaCl, 0.5% glucose, diaminosuccinic acid and 2% agar at pH 7.0. The diaminosuccinic acid may be present at any concentration which is sufficient to differentiate strains which are resistant to diaminosuccinic acid from strains which are sensitive to diaminosuccinic acid. For example, growth on plates containing diaminosuccinic acid at from about 0.5 g/L to about 50 g/L, preferably from about 1 g/L to about 10 g/L, and more preferably at about 2.5 g/L indicates that the strain is resistant to diaminosuccinic acid. The colonies are replica plated on minimal plates containing 5.0% fructose, 1.4% ammonium sulfate, 0.2% potassium dihydrogen phosphate, 0.1% magnesium sulfate, a sufficient amount of any additional compounds required by the microorganism to permit growth, and 2% agar at pH 7.3 with or without diaminosuccinic acid at the concentration used in the complete agar plates in order to identify colonies which are resistant to diaminosuccinic acid. Strains which grow in the presence of diaminosuccinic acid may be used in conjunction with the present invention.

To select a microorganism which is resistant to L-glutamic acid, the microorganism is mutagenized as described above. After mutagenesis, the cells are streaked on complete agar plates comprising 1% yeast extract, 1% peptone, 0.3% beef broth, 0.5% NaCl, 0.5% glucose, L-glutamic acid and 2% agar at pH 7.0. The L-glutamic acid may be present at any concentration which is sufficient to differentiate strains which are resistant to L-glutamic acid from strains which are sensitive to L-glutamic acid. For example, growth on plates containing L-glutamic acid at from about 50 mM to about 500 mM, preferably from about 100 mM to about 300 mM, and more preferably at about 240 mM indicates that the strain is resistant to L-glutamic acid. The colonies are replica plated on minimal plates containing 5.0% fructose, 1.4% ammonium sulfate, 0.2% potassium dihydrogen phosphate, 0.1% magnesium sulfate, a sufficient amount of any additional compounds required by the microorganism to permit growth, and 2% agar at pH 7.3 with or without L-glutamic acid at the concentration used in the complete agar plates in order to identify colonies which are resistant to L-glutamic acid. Strains which grow in the presence of L-glutamic acid may be used in conjunction with the present invention.

To select a microorganism which is resistant to L-threonine, the microorganism is mutangenized as described above. After mutagenesis, the cells are streaked on complete agar plates comprising 1% yeast extract, 1% peptone, 0.3% beef broth, 0.5% NaCl, 0.5% glucose. L-threonine and 2% agar at pH 17.0. The L-threonine may be present at any concentration which is sufficient to differentiate strains which are resistant to L-threonine from strains which are sensitive to L-threonine. For example, growth on plates containing L-threonine at from about 1% to about 13%, preferably from about 3% to about 10%, and more preferably at about 7% indicates that the strain is resistant to L threonine. The colonies are replica plated on minimal plates containing 5.0% fructose, 1.4% ammonium sulfate, 0.2% potassium dihydrogen phosphate, 0.1% magnesium sulfate, a sufficient amount of any additional compounds required by the microorganism to permit growth, and 2% agar at pH 7.3 with or without 1-threonine at the concentration used in the complete agar plates in order to identify colonies which are resistant to L-threonine. Strains which grow in the presence of L-threonine may be used in conjunction with the present invention.

To select a microorganism which is resistant to L-threonine fermentation mother liquid, the microorganism is mutagenized as described above. After mutagenesis, the cells are streaked on complete agar plates comprising 1% yeast extract, 1% peptone, 0.3% beef broth, 0.5% NaCl, 0.5% glucose, L-threonine fermentation mother liquid and 2% agar at pH 70. The L-threonine fermentation mother liquid may be present at any concentration which is sufficient to differentiate strains which are resistant to L-threonine fermentation mother liquid from strains which are sensitive to L-threonine fermentation mother liquid. For example, the plates may contain from about 20 to about 80%, more preferably from aobut 40 to about 70%, and in particular 60% L-threonine fermentation mother liquid. The colonies are replica plated on minimal plates containing 5.0% fructose, 1.4% ammonium sulfate, 0.2% potassium dihydrogen phosphate, 0.1% magnesium sulfate, a sufficient amount of any additional compounds required by the microorganism to permit growth, and 2% agar at pH 7.3 with or without L-threonine fermentation mother liquid at the concentration used in the complete agar plates in order to identify colonies which are resistant to L-threonine fermentation mother liquid. Strains which grow in the presence of L-threonine fermentation mother liquid may be used in conjunction with the present invention.

To select a microorganism which is resistant to azetidine, the microorganism is mutagenized as described above. After mutagenesis, the cells are streaked on complete agar plates comprising 1% yeast extract, 1% peptone, 0.3% beef broth, 0.5% NaCl, 0.5% glucose, azetidine and 2% agar at pH 7.0. The azetidine may be present at any concentration which is sufficient to differentiate strains which are resistant to azetidine from strains which are sensitive to azetidine. For example, growth on plates containing azetidine at from about 0.5 g/ℓ to about 5 g/ℓ, preferably from about 1 g/ℓ to about 3 g/ℓ, and more preferably at about 2 g/ℓ indicates that the strain is resistant to azetidine. The colonies are replica plated on minimal plates containing 5.0% fructose, 1.4% ammonium sulfate, 0.2% potassium dihydrogen phosphate, 0.1% magnesium sulfate, a sufficient amount of any additional compounds required by the microorganism to permit growth, and 2% agar at pH 7.3 with or without azetidine at the concentration used in the complete agar plates in order to identify colonies which are resistant to azetidine. Strains which grow in the presence of azetidine may be used in conjunction with the present invention.

To select a microorganism which is resistant to dehydroproline, the microorganism is mutagenized as described above. After mutagenesis, the cells are streaked on complete agar plates comprising 1% yeast extract, 1% peptone, 0.3% beef broth, 0.5% NaCl, 0.5% glucose, dehydroproline and 2% agar at pH 7.0. The dehydroproline may be present at any concentration which is sufficient to differentiate strains which are resistant to dehydroproline from strains which are sensitive to dehydroproline. For example, growth on plates containing dehydroproline at from about 0.5 g/ℓ to about 5 g/ℓ, preferably from about 1 g/ℓ to about 3 g/ℓ, and more preferably at about 2 g/ℓ indicates that the strain is resistant to dehydroproline. The colonies are replica plated on minimal plates containing 5.0% fructose, 1.4% ammonium sulfate 0.2% potassium dihydrogen phosphate, 0.1% magnesium sulfate, a sufficient amount of any additional compounds required by the microorganism to permit growth, and 2% agar at pH 7.3 with or without dehydroproline at the concentration used in the complete agar plates in order to identify colonies which are resistant to azetidine. Strains which grow in the presence of dehydroproline may be used in conjunction with the present invention.

To select a microorganism which is sensitive to fluoropyruvate, the microorganism is mutagenized as described above. After mutagenesis, the cells are streaked on complete agar plates comprising 1% yeast extract, 1% peptone, 0.3% beef broth, 0.5% NaCl, 0.5% glucose, and 2% agar at pH 7.0. The colonies are replica plated on minimal plates containing 5.0% fructose, 1.4% ammonium sulfate, 0.2% potassium dihydrogen phosphate, 0.1% magnesium sulfate, a sufficient amount of any additional compounds required by the microorganism to permit growth, and 2% agar at pH 7.3 with or without fluoropyruvate. The fluoropyruvate may be present at any concentration which is sufficient to differentiate strains which are sensitive to fluoropyruvate from strains which are resistant to fluoropyruvate. For example, lack of growth on plates containing fluoropyruvate at from about 10 mM to about 200 mM, preferably from about 20 mM to about 100 mM, and more preferably at about 40 mM indicates that the strain is sensitive to fluoropyruvate. Strains which grow in absence of fluoropyruvate but not in the presence of fluoropyruvate may be used in conjunction with the present invention.

It will be appreciated that each of the above selection procedures need not be performed in individual steps. Instead, after mutagenesis, the microorganisms may be plated on complete agar which selects for more than one characteristic simultaneously. For example, two or more characteristics may be simultaneosly selected. For example, to select cells which are resistant to a-methylserine, diaminosuccinic acid, L-glutamic acid, L-threonine, L-threonine fermentation mother liquid, azetidine, and dehydroproline, these each of these compositions may be included in the complete agar plates on which the mutagenized cells are streaked at the concentrations provided above. Thereafter, the mutagenized cells may be plated on minimal agar plates containing each of those compositions at the concentrations provided above.

It will also be appreciated that mutagenesis need not be separately performed for each characteristic to be selected. Rather, after mutagenesis, microorganisms which have a desired characteristic may be identified as provided above. Thereafter, the identified microorganisms may be selected for additional desired characteristics as described above.

As shown in Table 1, the novel strain KCCM-10168 is resistant to 60% of L-threonine fermentation mother liquid, 2 g/ℓ azetidine and 2 g/ℓ dehydroproline. As shown in Table 2, KCCM-10168 retains most of the characteristics of the parent strain, including a requirement for L-methione and resistance to L-threonine and L-glutamic acid. However, unlike the parent strain, KCCM-10168 is isoleucine-leaky and does not require diaminopimelic acid.

TABLE 1

Growth of the novel strain KCCM-10168 in the broths containing 60% of L-threonine fermentation mother liquid, azetidine and dehydroproline.

| Concentration | | | Strains | |
|---|---|---|---|---|
| L-threonine fermentation mother liquid (%) | Azetidine (g/l) | Dehydroproline (g/l) | Parent strain (KCCM-10132) | novel strain DSM9906 (KCCM-10168) |
| 0 | 0 | 0 | 1.804 | 1.821 |
| 60 | 1 | 1 | 0.053 | 1.675 |
|  | 2 | 2 | 0.048 | 1.587 |
|  | 4 | 4 | 0.049 | 0.501 |
| 80 | 1 | 1 | 0.058 | 0.092 |
|  | 2 | 2 | 0.064 | 0.089 |
|  | 4 | 4 | 0.059 | 0.077 |

Note: Growth of the strains was measured by absorbance at 610 nm after culturing them for 24 hours in minimal broth containing above three compounds.

TABLE 2

The comparison of the characteristics of DSM9906(KCCM-10168) and Parent strain (KCCM-10132).

| Concentration | | | | | | Strains | | | |
|---|---|---|---|---|---|---|---|---|---|
| | | | | | | Parent strain (KCCM-10132) | | DSM9906 (KCCM-10168) | |
| L-Met (mg/l) | L-Ile (mg/l) | DAPA (mg/l) | Fer. Liquid 60% | Azeti. | De Hydro proline | Min. broth | Complete broth | Min. broths | Complete broth |
| 200 | – | – | – | – | – | – | +++ | + | +++ |
| – | 200 | – | – | – | – | – | +++ | – | +++ |
| 200 | 200 | – | – | – | – | + | +++ | +++ | +++ |
| 200 | 200 | 100 | – | – | – | +++ | +++ | +++ | +++ |
| 200 | 200 | 100 | add | 2 g/l | 2 g/l | – | + | +++ | +++ |

Note: Growth state after being cultured in broth containing above six compounds. (–: no growth, +: growth, ++: good growth, +++: very good growth)

The growth and yield of L-threonine obtained with DSM9906 (KCCM-10168) was compared to those obtained with the parent strain KCCM-10132 at different glucose concentrations and the results are shown in Table 3. As shown in Table 3, KCCM-10168 provided a greater yield of L-threonine than KCCM-10132 in a high concentration of glucose.

TABLE 3

Comparison of the growth and productivity between DSM9906 (KCCM-10168) and KCCM-10132.

| | | Strains | |
|---|---|---|---|
| L-Glu Conc. | | KCCM-10132 | DSM9906 (KCCM-10168) |
| 5.0% | Growth[1] | 0.555 | 0.567 |
|  | L-threonine[2] | 12.53 | 12.61 |
| 7.0% | Growth | 0.608 | 0.613 |
|  | L-threonine | 16.92 | 17.34 |
| 10.0% | Growth | 0.852 | 0.866 |
|  | L-threonine | 19.86 | 22.97 |
| 12.5% | Growth | 0.590 | 0.861 |
|  | L-threonine | 13.09 | 22.23 |

TABLE 3-continued

Comparison of the growth and productivity between DSM9906 (KCCM-10168) and KCCM-10132.

| | Strains | |
|---|---|---|
| L-Glu Conc. | KCCM-10132 | DSM9906 (KCCM-10168) |

Note[1]: 50-fold diluted solutions of the cultures incubated for 36~72 hours in production media (Example 1) were measured by absorbance at 610 nm (Beckman DU-70)
Note[2]: L-threonine accumulated in cultures was measured using an automatic amino acid analyzer (Hitachi L-8500A)

Example 1

Production of L-threonine Using DSM9906 (KCCM-10168)

Strain used: DSM9906 (KCCM-10168)

Pre-culture medium composition: Glucose 0.5%, Yeast Extract 1.0%, Peptone 1.0%, NaCl 0.5%, Beef broth 0.3%, pH 7.0.

Production medium composition: Glucose 12.5%, Corn steep liquor 3%, Potassium dihydrogen phosphate 0.1%, Ferrous sulfate 2 mg/ℓ, Manganese sulfate 2 mg/ℓ, Ammonium sulfate 0.5%, L-Methionine 200 mg/ℓ and Calcium carbonate 5%(separately sterilized), pH 7.0. In the case of the parent strain KCCM-10132, L-Isoleucine was added at 200 mg/ℓ.

Pre-Culturing 5 μm of the pre-culture medium was aliquoted to 18φ×185 mm test tubes and autoclaved at 121° C. for 15 min. under pressure. After being cooled, the aliquots were inoculated with the novel strain DSM9906 (KCCM-10168) by use of a sterilized metal loop. They were incubated at 30° C. for 20 hours with shaking at 120 cycles per min.

Production Culturing: 70 ml aliquots of the threonine production media were placed in 500 ml Sakaguchi flasks and autoclaved at 121° C. for 15 min. under pressure. After being cooled, the aliquots of the autoclaved threonine production media were inoculated with the pre-cultures of DSM9906(KCCM-10168) at a level of 1%. The strain was incubated at 30° C. for 72 hours with shaking at 120 cycles per min. After fermentation, L-threonine was found to be accumulated at an amount of 22.23 mg/ml in the novel strain DSM9906(KCCM-10168) culture. When the above procedure was performed using the parent strain KCCM-10132, L-threonine was found to be accumulated at an amount of 13.09 mg/ml.

Example 2

Strain used: DSM9906 (KCCM-10168).

Primary pre-culture medium composition: Same as the Pre-culture medium composition of Example 1.

Secondary Pre-culture medium composition: Glucose 2%, Corn steep liquor 3%, Potassium dihydrogen phosphate 0.1%, Ferrous sulfate 2 mg/ℓ, Manganese sulfate 2 mg/ℓ, Ammonium sulfate 0.05%, Urea 0.6%, L-Methionine 200 m/ℓ, pH 7.0.

Production medium composition: Glucose 10%, Corn steep liquor 3%, Potassium dihydrogen phosphate 0.1%, Ferrous sulfate 2 mg/ℓ, Manganese sulfate 2 mg/ℓ, Ammonium sulfate 0.05%, Urea 0.6%, L-Methionine 200 mg/ℓ and pH 7.0. In the case of the parent strain KCCM-10132, L-Isoleucine was added at 200 mg/ℓ.

Pre-Culturing: A primary pre-culture of DSM9906(KCCM-10168) was obtained in the same manner as that of Example 1. It was inoculated at 1% in 50 ml aliquots of the secondary pre-culture media in Sakaguchi flasks, which had been autoclaved at 121° C. for 15 min. Incubation was carried out at 30° C. for 24 hours with shaking at 120 cycles per min, to give a secondary pre-culture.

Production Culturing: 2 l of the production media were bottled in a 5 l fermentation bath and then autoclaved at 121° C. for 15 min. under pressure. The secondary culture of DSM9906 (KCCM-10168) was inoculated at 5–10% and incubated at 30° C. for 100 hours with aeration at 0.8–1.5 vvm and stirring at 550 rpm. Glucose were added so as to maintain the glucose concentration of the media at 1–3%. The media were adjusted into pH 6.5~7.0 with ammonia water. After fermentation, L-threonine was found to be accumulated at an amount of 110.20 mg/ml in the DSM9906 (KCCM-10168) culture. In the same manner as the above, L-threonine was produced from the parent strain KCCM-10132 and measured to be 95.24 mg/ml. 1 l of each of the cultures was centrifuged to harvest the bacteria. The supernatant was passed through an ion exchange resin to adsorb L-threonine, eluted and purified to yield L-threonine crystals at an amount of 104.7 mg/ml from the culture of DSM9906 and 90.5 mg/ml from the culture of KCCM-10132. L-Isoleucine 200 mg/ml was added in the secondary pre-culture medium and production culturing of the parent strain KCCM-10132.

What is claimed is:

1. An L-threonine-producing microorganism having characteristics comprising: requirement of L-threonine for growth; L-isoleucine-leaky for growth; resistance to αmethylserine, diaminosuccinic acid, L-glutamic acid, L-threonine, fermentation mother liquid containing L-threonine, azetidine and dehydroproline; and susceptibility to fluoropyruvate, wherein said microorganism is a strain of *Escherichia coli*, and wherein said microorganism has the Korean Culture Center of Microorganisms deposit number KCCM-10168.

2. An L-threonine-producing microorganism having characteristics comprising: requirement of L-methionine for growth; L-isoleucine-leaky for growth; resistance to αmethylserine, diaminosuccinic acid, L-glutamic acid, L-threonine, fermentation mother liquid containing L-threonine, azetidine and dehydroproline; and susceptibility to fluoropyruvate, wherein said microorganism is a strain of *Escherichia coli*, and wherein said microorganism has all the characteristics of the microorganism having the Korean Culture Center of Microorganism deposit number KCCM-10168.

* * * * *